(12) United States Patent
Mennen et al.

(10) Patent No.: US 6,392,096 B1
(45) Date of Patent: May 21, 2002

(54) PROCESS FOR THE PREPARATION OF UREA

(75) Inventors: Johannes H Mennen, Roggel; Kees Jonckers, Susteren, both of (NL)

(73) Assignee: DSM N.V., Heerlen (NL)

( * ) Notice: Subject to any disclaimer, the term of this patent is extended or adjusted under 35 U.S.C. 154(b) by 0 days.

(21) Appl. No.: 09/902,467

(22) Filed: Jul. 11, 2001

Related U.S. Application Data (63) Continuation of application No. PCT/NL00/00044, filed on Jan. 20, 2000.

(30) Foreign Application Priority Data

Jan. 25, 1999 (NL) .............................................. 1011123

(51) Int. Cl.$^7$ ............................................. C07C 273/04
(52) U.S. Cl. ............................. 564/70; 564/67; 564/68; 564/69; 564/71; 564/72; 564/73
(58) Field of Search ............................... 564/67, 68, 69, 564/70, 71, 72, 73

(56) References Cited

FOREIGN PATENT DOCUMENTS

| EP | 0 329 215 A | 8/1989 |
|---|---|---|
| EP | 0 834 501 A | 4/1998 |

*Primary Examiner*—Peter O'Sullivan
(74) *Attorney, Agent, or Firm*—Pillsbury Winthrop LLP (57) ABSTRACT

The invention relates to a process for the preparation of urea from ammonia and carbon dioxide, the preparation being effected in whole or in part in a vertical combi-reactor. The gas stream leaving the stripper is fed to the condenser section of a vertical combi-reactor in which this gas stream is wholly or partially condensed in the carbamate stream which is transferred from the scrubber section to the condenser section via a downcomer. Ammonia and carbon dioxide are partially converted into urea in this condenser section of the combi-reactor. The urea conversion is completed in the reaction section of the combi-reactor.

15 Claims, 5 Drawing Sheets

PROCESS FOR THE PREPARATION OF UREA

CROSS-REFERENCE TO RELATED APPLICATIONS

This Application is a continuation of International Application PCT/NL00/00044, filed Jan. 20, 2000, which designated the U.S. and was published in the English language.

The invention relates to a process for the preparation of urea from ammonia and carbon dioxide.

Urea can be prepared by introducing ammonia and carbon dioxide into a synthesis zone at a pressure of between 12 and 40 MPa and at a temperature of between 150 and 250° C. Urea formation might best be represented here by two consecutive reaction steps with ammonium carbamate being formed in the first step according to the exothermic reaction:

$$nNH_3 + CO_2 \rightarrow H_2N\text{---}CO\text{---}ONH_4 + (n-2)NH_3$$

Dehydration in the second step of the ammonium carbamate formed then results in the formation of urea according to the endothermic equilibrium reaction:

$$H_2N\text{---}CO\text{---}ONH_4 \rightarrow H_2N\text{---}CO\text{---}NH_2 + H_2O$$

The extent to which these reactions proceed depends on, among other factors, the temperature and the excess ammonia used. A solution that consists essentially of urea, water, unbound ammonia and ammonium carbamate is obtained as reaction product. The ammonium carbamate and the ammonia are removed from the solution and are preferably returned to the synthesis zone. In addition to the aforementioned solution, a gas mixture is formed in the synthesis zone, which consists of non-converted ammonia and carbon dioxide plus inert gases. Ammonia and carbon dioxide are removed from this gas mixture and are preferably also returned to the synthesis zone. The synthesis zone may comprise separate zones for the formation of ammonium carbamate and urea. These zones may, however, also be united in a single apparatus.

In practice, various processes are used for the preparation of urea. At first, urea was prepared in so-called conventional high-pressure urea plants, which at the end of the 1960s were succeeded by processes carried out in so-called urea stripping plants.

The conventional high-pressure urea plants that are currently still operating are understood to be urea plants in which the decomposition of the ammonium carbamate not converted into urea and the expulsion of the usual excess ammonia take place at a substantially lower pressure than the pressure in the synthesis reactor itself. In a conventional high-pressure urea plant the synthesis reactor is usually operated at a temperature of 180–250° C. and a pressure of 15–40 MPa. Furthermore, in a conventional high-pressure urea plant ammonia and carbon dioxide are fed directly to the urea reactor. In a conventional high-pressure urea process the molar $NH_3/CO_2$ ratio (=N/C ratio) in the urea synthesis lies between 3 and 6.

As regards the recycling of unconverted ammonia and carbon dioxide to the synthesis section, one can distinguish Once Through conventional urea plants(no recycle), Partial Recycle conventional urea plants (only a proportion of ammonia and/or carbon dioxide is recycled) and Total Recycle plants (both ammonia and carbon dioxide are recycled).

A urea stripping plant is understood to be a urea plant in which the decomposition of the ammonium carbamate that has not been converted into urea and the expulsion of the usual excess ammonia largely take place at a pressure that is essentially almost equal to the pressure in the synthesis reactor. This decomposition and expulsion take place in one or more stripper(s) installed downstream of the synthesis reactor with the aid of a stripping gas, such as, for example, carbon dioxide and/or ammonia, and with addition of heat. It is also possible to apply thermal stripping. Thermal stripping means that ammonium carbamate is decomposed and the ammonia and carbon dioxide present are removed from the urea solution exclusively by means of the supply of heat. The ammonia is and carbon dioxide-containing gas stream exiting from s the stripper is condensed in a high-pressure carbamate condenser.

The gas mixture that has not reacted in the urea synthesis is vented from the synthesis section. In addition to the condensable ammonia and carbon dioxide, this gas mixture (reactor vent gas) also contains inert gases. The condensable components (ammonia and carbon dioxide) can be absorbed, for example, in a high-pressure scrubber at synthesis pressure, before the inert gases are vented. In such a high-pressure scrubber the condensable components, ammonia and carbon dioxide, are preferably absorbed from the reactor vent gas into the low-pressure carbamate stream formed in the further recovery. The carbamate stream from the high-pressure scrubber, which contains the ammonia and carbon dioxide absorbed from the reactor vent gas, is returned to the synthesis whether or not via the high-pressure carbamate condenser. The reactor, high-pressure scrubber, stripper and high-pressure carbamate condenser are the most important elements of the high-pressure section of a urea stripping plant.

In a urea stripping plant the synthesis reactor is operated at a temperature of 160–240° C. and preferably at a temperature of 170–220° C. The pressure in the synthesis reactor is 12–21 MPa, preferably 12.5–19 MPa. The N/C ratio in the synthesis of a stripping plant lies between 2.5 and 5. The synthesis can be carried out in a single reactor or in a plurality of reactors arranged in parallel or in series. When use is made of two reactors in parallel, the first reactor can be operated using virtually fresh raw materials and the second using raw materials entirely or partly recycled, for example from the urea recovery.

A frequently used embodiment for the preparation of urea according to a stripping process is the Stamicarbon $CO_2$-stripping process as described in European Chemical News, Urea Supplement, of Jan. 17, 1969, pages 17–20.

The high-pressure carbamate condenser in a Stamicarbon CO2 stripping process is preferably designed as a so-called submerged condenser as described in NL-A-8400839. The submerged condenser can be installed in horizontal or vertical position. It is, however, particularly advantageous to carry out the condensation in a horizontal submerged condenser (a so-called pool condenser; see for example Nitrogen No 222, July–August 1996, pp. 29–31), because, in comparison with other designs of this condenser, the liquid generally has a longer residence time in the pool condenser. This results in the formation of extra urea in the pool condenser. The amount of urea formed in the pool condenser is higher than 30% of the theoretically possible amount of urea formed.

After the stripping treatment, the pressure of the stripped urea synthesis solution is reduced in the urea recovery and the solution is evaporated, after which urea is recovered. This produces a low-pressure carbamate stream in the recovery. This low-pressure carbamate stream is preferably returned via the high-pressure scrubber to the section operating at synthesis pressure.

In the high-pressure carbamate condenser the gas stream from the stripper condenses in the carbamate stream coming from the high-pressure scrubber. The carbamate solution coming from the high-pressure carbamate condenser is preferably passed to the synthesis reactor together with the ammonia needed for the reaction.

In a particular embodiment of a urea stripping process the functions of the reactor, pool condenser and high-pressure scrubber are combined in a single high-pressure vessel with the functionalities of these process steps being separated in this high-pressure vessel by low-pressure internals designed for small pressure differences. An example of such an embodiment is described in Nitrogen No. 222, July–August 1996, pages 29–31, which describes the poolreactor, as does U.S. Pat. No. 5,767,313. This poolreactor preferably is placed in horizontal position.

The aim of the present invention is to provide an improved process for the preparation of urea, which also entails lower investment costs.

The applicant has found an improved process for the preparation of urea from ammonia and carbon dioxide, which is characterised in that the preparation takes place wholly or partly in a vertical combi-reactor.

This combi-reactor is comprised of a condenser section, reactor section and scrubber section, with the condenser section most usually being located beneath the reactor section and the scrubber section being placed above the reactor section. The conditions of temperature and pressure in the reactor, scrubber and condenser are virtually equal and are such that the combi-reactor is operated at high pressure. The pressure preferably is between 12 and 22 MPa, in particular between 13 and 21 MPa. The temperature is between 150 and 250° C., preferably between 170 and 200° C. The process for the preparation of urea from ammonia and carbon dioxide is characterised herein that the gas stream coming from the stripper is fed to the condenser section of a vertical combi-reactor. In particular, this gas stream is wholly or partly condensed in the carbamate stream which passes from the scrubber into the condenser section through a downcomer. The condenser preferably is of the submerged type. The gas stream coming from the stripper consists essentially of ammonia and carbon dioxide. The stripping gases are distributed, with the aid of for example a gas divider, in the bottom of the condenser and are wholly or partially condensed in the carbamate originating from the scrubber via a downcomer.

The gas/liquid mixture which evolves subsequently passes through the condenser tubes, where the exothermic carbamate reaction takes place. Low-pressure steam is formed around the tubes as a result of the heat released in this exothermic carbamate reaction. A proportion of the carbamate formed can be returned to the bottom of the condenser section with the aid of a funnel.

Carbamate circulates in the condenser section as a result of the density difference between the carbamate stream in the downcomer and the carbamate/gas mixture in the tubes. This ensures intimate mixing of the carbamate in the condenser section and generates turbulence, which is favourable for heat transfer. Residence time for the liquid carbamate in the condenser is provided by designing this condenser as a submerged condenser so that urea formation partly takes place already here.

The remaining carbamate coming from the condenser, along with the inerts and unconverted ammonia and carbon dioxide, are passed to the reactor section of the combi-reactor together with the urea that has already formed and water. The remaining part of the endothermic urea reaction takes place in this reactor section. The heat required is supplied by the exothermic carbamate reaction between unconverted ammonia and carbon dioxide from the condenser.

The reactor section is preferably designed as a high-pressure bubble column. This reactor section is preferably provided with means which ensure that the liquid flows through the reactor substantially in plug flow. To that end, this reactor section is divided, preferably by means of sieve trays, into compartments of virtually equal capacity, so that the reactor is a cascade-type reactor and hence plug flow is approached. The sieve trays used may be of any one of the types described in the literature on urea production. The urea solution is passed to a downstream reactor or to a downstream gas/liquid separator.

The inerts, which still contain free ammonia and carbon dioxide, are washed in the scrubber section with the low-pressure carbamate stream evolving in the further recovery. Unconverted ammonia and carbon dioxide may be washed out either in whole or part in this scrubber. The inerts may be cleared of any remaining ammonia and carbon dioxide outside the combi-reactor.

The combi-reactor may be used in grassroots plants and in existing plants.

The invention also relates to a method of improving and optimising (revamping) existing urea plants by addition of a combi-reactor. Such addition may take place in conventional plants and stripping plants.

The combi-reactor is a vertical reactor and, as a result of such vertical positioning, the reactor requires only limited floor area. The available floor area often is limited especially in revamping projects, for which reason the combi-reactor is particularly suitable here. The combi-reactor also is an attractive alternative to, for example, the poolreactor.

The combi-reactor may be employed in conventional urea plants for revamping projects in Once Through, Partial Recycle or Total Recycle plants. In the case of revamps of conventional urea plants it is preferred to add, besides the combi-reactor, a stripper and a gas/liquid separator.

The advantage of the combi-reactor in revamping conventional plants is the fact that capacity increases of 1500 to 4000 tonnes a day can be achieved with steam consumption being comparable to the steam consumption in stripping plants, i.e. about 925 kg of steam per tonne of urea. This is a remarkable improvement for a conventional urea plant. The combi-reactor affords the possibility of adding both condenser capacity and reaction volume to the existing synthesis.

In revamping projects the combi-reactor is operated at a pressure which is somewhat lower than the pressure in the downstream existing reactor. The driving force needed for the reaction solution to flow from the combi-reactor to the downstream reactor is supplied by a high-pressure ammonia ejector. In this way, the combi-reactor may be placed at ground level.

The urea reaction is completed in the downstream existing reactor. To the downstream urea reactor is added, if necessary for process reasons, a small proportion of the fresh carbon dioxide which is needed for the exothermic carbamate reaction to proceed in this reactor, which reaction supplies the heat needed for the endothermic reaction. In the case of revamping projects in conventional urea plants, the urea solution is passed to a high-pressure stripper and preferably a high-pressure $CO_2$ stripper to be newly installed, in which the unconverted carbamate dissociates into ammonia and carbon dioxide. Fresh stripping gases and preferably fresh carbon dioxide and heat are employed for such dissociation. The evolving stripping gases are discharged to the combi-reactor along with the vapour evolving in the downstream existing urea reactor.

The revamping principle for stripping plants is essentially the same as that described above for revamping conventional urea plants. Here, too, the existing reactor functions as downstream urea reactor and the high-pressure ammonia ejector is the driving force to overcome the pressure difference between the combi-reactor and the existing reactor. In this way, the combi-reactor may be placed at ground level in stripping units too. However, a stripper and gas/liquid separator need not be added in stripping plants. Here again the combi-reactor affords the possibility of adding condenser capacity and reaction volume to the existing synthesis, increasing the capacity of stripping plants to 4000 tonnes per day or more, without increased steam consumption per tonne of urea produced.

Essentially, the existing high-pressure carbamate condenser, which may be a falling-film type condenser or a submerged condenser, may be incorporated in this design. This revamping technique for stripping plants may also be employed for $CO_2$ stripping plants and $NH_3$ stripping plants as well as for stripping plants in which thermal stripping is applied.

The principle of grassroots plants with a combi-reactor is essentially the same as that described for the revamping of conventional urea plants. However, a downstream reactor is not needed in grassroots plants inasmuch as the urea reaction can go to completion already in the reaction section of the combi-reactor.

The invention also relates to a urea plant in which the high-pressure section substantially consists of a combi-reactor, a gas/liquid separator and a stripper, preferably a $CO_2$ stripper.

Since in grassroots plants the combi-reactor is also placed at ground level, the urea discharged is passed to gas/liquid separator via a high-pressure ammonia ejector. The liquid discharge of this separator is sent to a high-pressure $CO_2$ stripper in which the unconverted carbamate dissociates. The stripping gases which also contain the fresh carbon dioxide along with the off-gases from the downstream separator are discharged to the condenser section of the combi-reactor.

A major advantage of the process of the invention is that it can be embodied in a plant with substantially lower investment costs because the integration of a heat exchanger/condenser and scrubber in a reactor requires fewer items of equipment and piping, which must be resistant to high pressures in a highly corrosive environment. A further advantage is the installation at ground level, resulting in a lower plant structure. This offers further advantages in terms of investment and affords improved safety.

The conversion of carbamate into urea and water can be effected by providing for long enough a residence time for the reaction mixture in the combi-reactor. The residence time will in general be longer than 10 min, preferably longer than 20 min. The residence time will in general be shorter than 2 hours, preferably shorter than 1 hour. At a higher temperature and pressure in the combi-reactor, a shorter residence time will usually suffice to obtain high conversion.

The combi-reactor generally is designed as a wide pipe with a diameter of between 1 and 5 meters, preferably between 2 and 4 m. The length of the combi-reactor generally is between 5–60 meters, preferably between 10 and 40 meters.

The combi-reactor generally is provided with means that ensure that the liquid flows through the reactor substantially in plug flow. To this end the reactor is provided with for example a structured packing (in one or more locations) or with baffles that divide the reactor into compartments. The compartments form a succession of continuously stirred tank reactors (CSTRs), as it were. CSTRs and compartments will henceforth be referred to on a number of occasions for a good understanding of the invention. The use of these terms is not meant to limit the invention thereto.

The number of compartments in the combi-reactor as series-arranged CSTRs preferably is greater than 2, in particular greater than 5. The number of compartments as CSTR will in general be less than 40, preferably less than 20.

The compartments in the combi-reactor are preferably formed by virtually horizontal baffles. The surface area of such baffles preferably is not less than 50%, preferably not less than 85%, of the horizontal cross-sectional area of the vertical reactor. The surface area of the baffles preferably is practically 100% of the horizontal section of the reactor placed in vertical position.

The heat released in the reactor can be carried off by water passing through the heat exchanger tubes, in which process the water is converted into low-pressure steam of 3–10 bar, preferably 4–7 bar. The heat may also be carried of by passing through a process stream that needs to be heated, for example a urea solution to be concentrated at 2–8 bar or a urea solution to be expanded at 15–40 bar. The heat exchanger is installed in the condenser section of the reactor. This section occupies 10–70%, preferably 20–50%, of the total length of the reactor.

The condensation zone and the heat exchanger of the combi-reactor preferably are designed as a so-called submerged condenser. Here, a portion of the gas mixture to be condensed passes through the tube side of a tubular heat exchanger, with a dilute carbamate solution passing through the shell side, the released heat of solution and condensation being carried off by a medium, for example water, flowing around the tubes, the water being converted into low-pressure steam.

The invention is explained in further detail by way of example with reference to the following figures, where FIG. 1 represents the state of the art and FIGS. 2 to 5 represent embodiments of the present invention.

Figure 1:
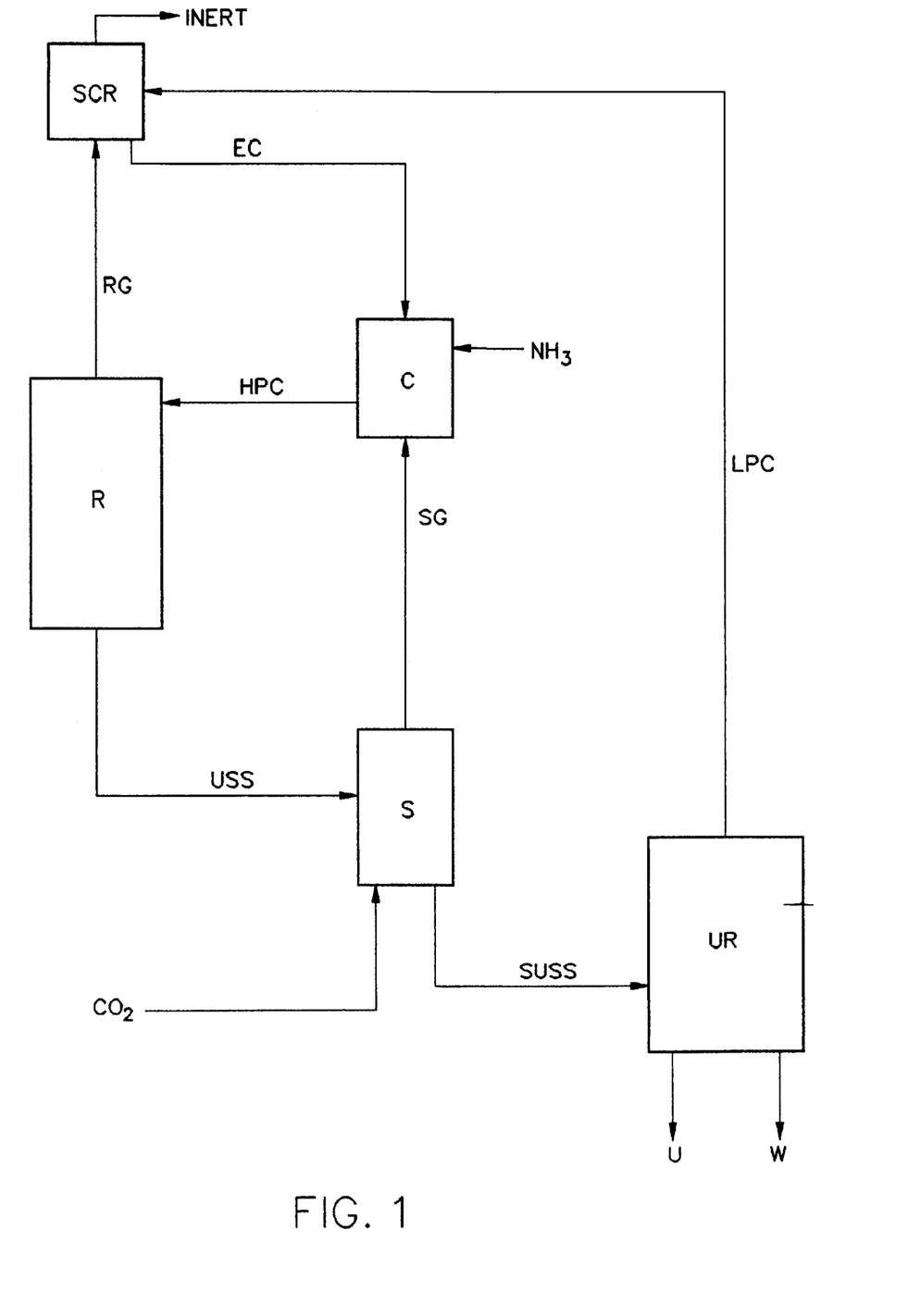
FIG. 1: a schematic representation of a section of a urea stripping plant based on the Stamicarbon $CO_2$ stripping process.

In FIG. 1, R represents a reactor in a Stamicarbon $CO_2$ stripping plant in which carbon dioxide and ammonia are converted into urea. The urea synthesis solution (USS) leaving the reactor is sent to a $CO_2$ stripper (S), in which the USS is converted into a gas stream (SG) and a liquid stream (SUSS) by stripping the USS with $CO_2$. The gas stream (SG) leaving the $CO_2$ stripper consists substantially of ammonia and carbon dioxide and the SUSS is the stripped USS. The stream containing the stripped urea synthesis solution SUSS is passed to the urea recovery (UR) where urea (U) is recovered and water (W) is discharged. A low-pressure ammonium carbamate stream (LPC) is obtained in the UR and is fed to a high-pressure scrubber (SCR). In this scrubber the LPC is contacted with the gas stream (RG) coming from the reactor and consisting substantially of ammonia and carbon dioxide as well as inerts (non-condensable components) present in the carbon dioxide feed and the ammonia feed. Normally heat is also transferred in the SCR. In this example, the enriched carbamate stream (EC) leaving the SCR is passed to the high-pressure carbamate condenser (C) in which the SG stream is condensed with the aid of EC. This condensation may also be effected without adding EC to C; in that case it is logical for EC to be added to the reactor R direct. The resulting high-pressure carbamate stream (HPC) is returned to the reactor. In this example, the fresh ammonia is recycled via the high-pressure carbamate condenser (C) but may of course be admitted elsewhere in the R→S→C→R loop or in the R→SCR→C→R loop.

Figure 2:
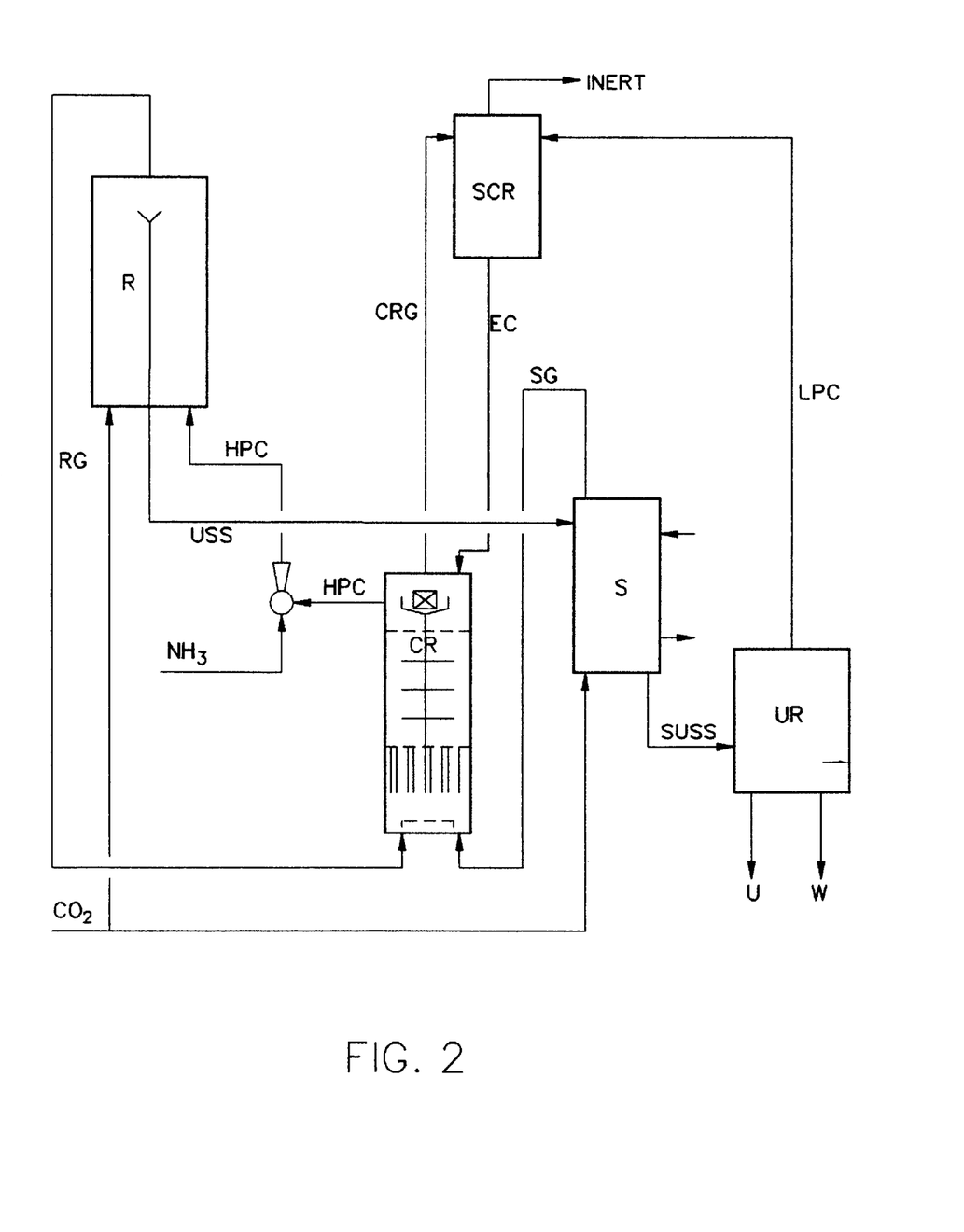
FIG. 2: A schematic representation of a section of a urea stripping plant based on the Stamicarbon $CO_2$ stripping process to which a combi-reactor is added.

In FIG. 2, R represents a reactor in a Stamicarbon $CO_2$ stripping plant in which carbon dioxide and ammonia are converted into urea. The urea synthesis solution (USS) leaving the reactor is passed to a $CO_2$ stripper (S) in which the USS is converted into a gas stream (SG) and a liquid stream (SUSS) by stripping the USS with $CO_2$. The gas stream (SG) leaving the $CO_2$ stripper consists substantially of ammonia and carbon dioxide and the SUSS is the stripped USS. The stream containing stripped urea synthesis solution SUSS goes to the urea recovery (UR) where urea (U) is recovered and water (W) is discharged.

A low-pressure ammonium carbamate stream (LPC) is obtained in the UR and is fed to a high-pressure scrubber (SCR). In this scrubber the LPC is contacted with the gas stream (CRG) coming from the combi-reactor and substantially consisting of ammonia and carbon dioxide as well as inerts (non-condensable components) present in the carbon dioxide feed and the ammonia feed. Heat may optionally be transferred in this high-pressure scrubber (SCR). The enriched carbamate stream (EC) leaving the SCR is passed to the scrubber section of the combi-reactor. The evolving high-pressure carbamate stream is contacted, via a downcomer, with the ammonia and gaseous carbon dioxide in the condenser section of the combi-reactor. The carbamate and the urea formed in this condenser section of the combi-reactor is passed to the reaction section of the combi-reactor. The urea solution, which also contains unconverted carbamate (HPC), is passed to the reactor (R) with the aid of an ejector which is powered by the ammonia necessary. The gas stream (RG) leaving the urea reactor (R), which consists essentially of ammonia and carbon dioxide as well as inerts, goes to the condenser section of the combi-reactor.

Figure 3:
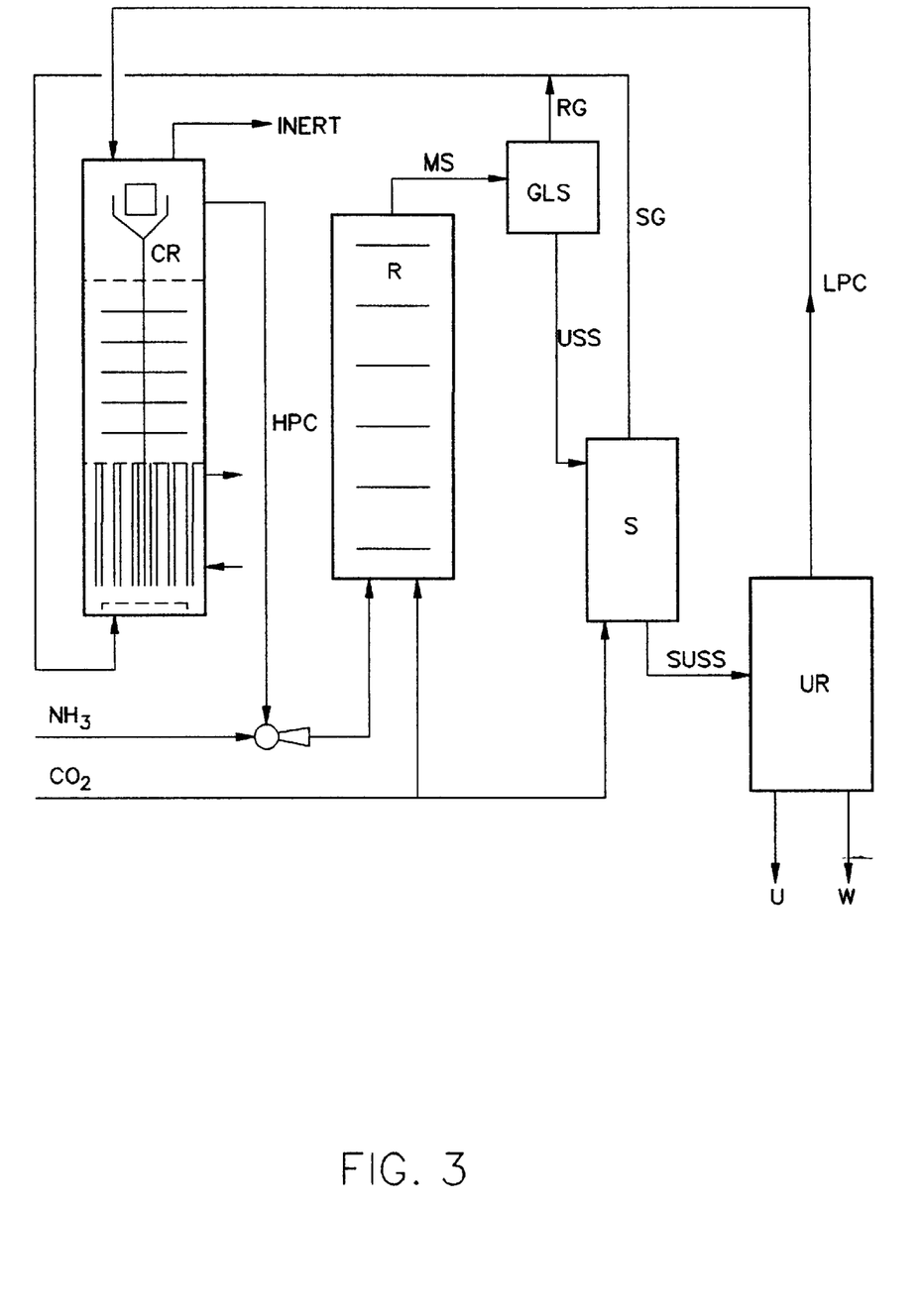
FIG. 3: A schematic representation of a section of urea plant based on the Conventional principle, incorporating a combi-reactor and a $CO_2$ stripper.

In FIG. 3, R represents a reactor in a conventional urea plant. The reaction product leaving the reactor goes as a mixed stream (MS) to the gas/liquid separator (GLS), where the reaction product is separated into a gas stream (RG) and a liquid stream (USS). This liquid stream, consisting essentially of urea, ammonium carbamate and water, is passed to the stripper (S) and is stripped with carbon dioxide with addition of heat. The stripper gas (SG) leaving the stripper is combined with gas stream (RG), both of which consist essentially of ammonia and carbon dioxide, and transferred to the condenser section of the combi-reactor. The stripped urea solution (SUSS) leaving the stripper is transferred to the urea recovery, where urea (U) is recovered and water (W) is recovered. In the urea recovery evolves also an aqueous low-pressure carbamate stream (LPC), which is passed to the scrubber section of the combi-reactor. The evolving high-pressure carbamate stream is contacted, via a downcomer, with the ammonia and gaseous carbon dioxide in the condenser section of the combi-reactor. The carbamate and the urea formed in this condenser section of the combi-reactor are passed to the reaction section of the combi-reactor. The urea solution, also containing unconverted carbamate (HPC), is passed to the reactor (R) with the aid of an ejector which is powered by the ammonia necessary.

Figure 4:
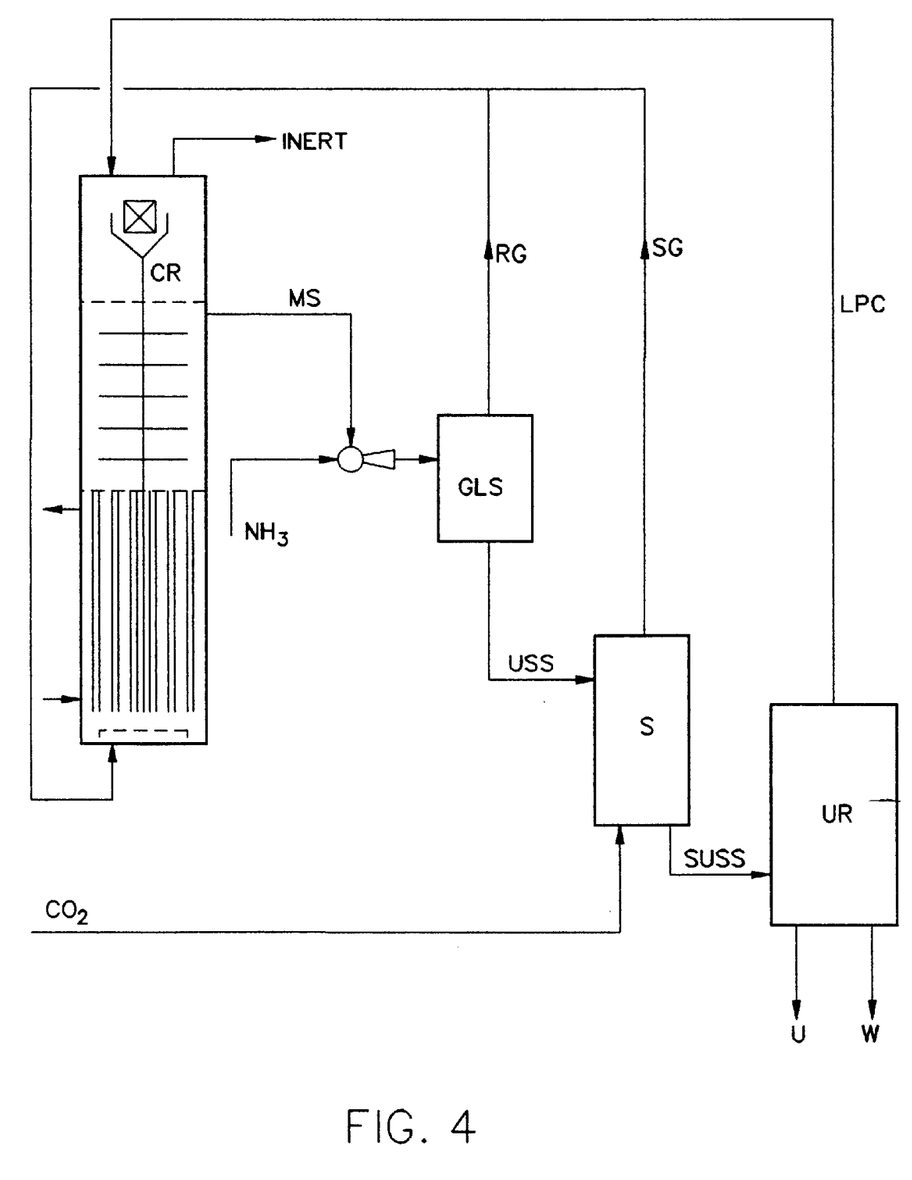
FIG. 4: A schematic representation of a section of a new urea stripping plant based on the combi-reactor principle.

In FIG. 4, CR is a schematic representation of a combi-reactor with condenser, reaction section and scrubber in a section of a new plant design. The reaction product evolving in the combi-reactor is transferred as a mixed stream (MS), with the aid of an ammonia-powered ejector, to a gas/liquid separator (GLS). Here, the reaction product is separated into a gas stream (RG) and a liquid stream (USS). The gas stream (RG) consists essentially of ammonia and carbon dioxide and the liquid stream (USS) consists essentially of water, ammonium carbamate and urea. The liquid stream (USS) is stripped in the stripper (S) with carbon dioxide with addition of heat. In this process evolves a gas stream (SG) consisting essentially of ammonia and carbon dioxide and a liquid stream (SUSS) consisting essentially of urea and water. The gas stream is passed to the condenser section of the combi-reactor together with the gas stream (RG). The urea solution (SUSS) is converted in the urea recovery into urea (U), water (W) and low-pressure ammonium carbamate (LPC). This low-pressure carbamate (LPC) goes to the scrubber section of the combi-reactor.

Figure 5:
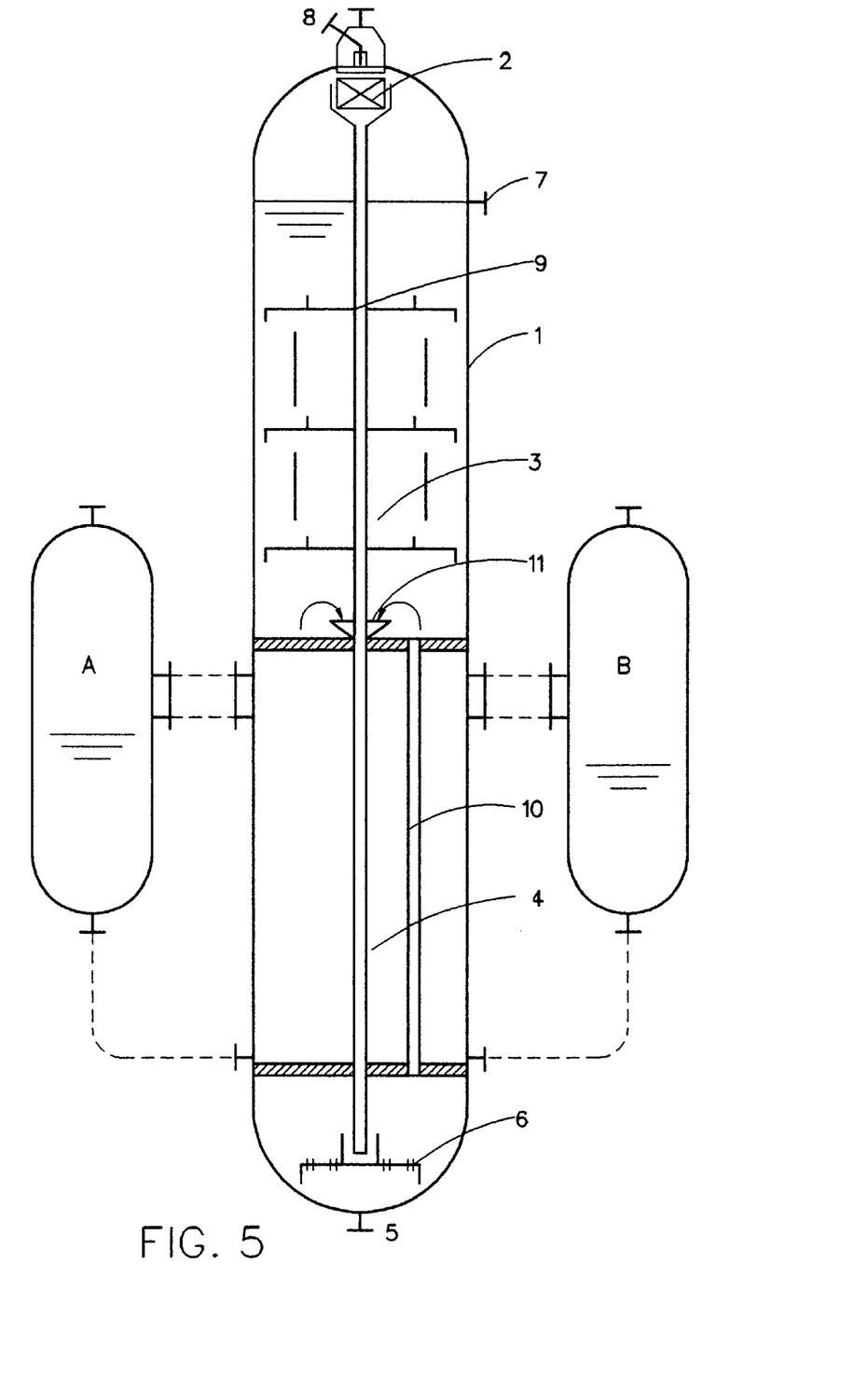
FIG. 5: A schematic representation of a section of a combi-reactor of the present invention.

FIG. 5 shows a schematic representation of an embodiment of the combi-reactor (CR). Here, 1 represents the wall of the combi-reactor, 2 the scrubber section, 3 the reactor section and 4 the condenser section. A and B are steam vessels. The gases (SG) leaving the stripper (S) enter the condenser at 5 and are distributed in the bottom of the condenser by gas divider 6. The reaction mixture leaves the combi-reactor as a mixed stream (Mg) through pipe 7. The low-pressure carbamate (LPC) from the urea recovery (UR) enters the combi-reactor at 8. Carbamate from the scrubber section enters the condenser section via downcomer 9. A tube of the submerged condenser section is represented by 10. 11 indicates a suitable location for a funnel, although a funnel is not necessary. This funnel ensures further circulation of liquid across the condenser section via the downcomer. This is advantageous in that it promotes heat transfer in the condenser section.

The invention is further illustrated by the following examples.

COMPARATIVE EXAMPLE A

Table 1 below presents the compositions in percent by weight of the various streams for a Stamicarbon $CO_2$ stripping plant as shown in FIG. 1. The compositions indicate that almost all urea is converted in the reactor (R) and that carbamate condenses in the high-pressure condenser (C).

TABLE 1

| Stream | Urea | $NH_3$ | $CO_2$ | $H_2O$ | Inert |
| --- | --- | --- | --- | --- | --- |
| USS | 33.0 | 30.5 | 18.0 | 18.5 | — |
| $CO_2$ | — | — | 96.0 | 0.5 | 3.5 |
| SUSS | 55.0 | 7.8 | 10.5 | 26.7 | — |
| SG | — | 41.0 | 54.5 | 3.5 | 1.0 |
| $NH_3$ | — | 99.6 | — | 0.4 | — |
| HPC | — | 49.5 | 42.0 | 8.0 | 0.5 |
| RG | — | 50.0 | 39.5 | 3.5 | 7.0 |
| EC | — | 39.0 | 39.0 | 22.0 | — |
| LPC | — | 30.0 | 37.0 | 33.0 | — |
| Inert | — | 5.5 | 5.0 | 0.5 | 89.0 |

EXAMPLE 1

Table 2 below presents the compositions in percent by weight of the various streams for a Stamicarbon $CO_2$ stripping plant in which a combi-reactor has been added to wholly or partially replace the high-pressure carbamate condenser (C) as shown in FIG. 2. The compositions of the streams indicate that a substantial part of the urea reaction takes place in the Combi-reactor and that a proportion or all of the carbamate condenses in the combi-reactor, too. The urea reaction which takes place in the combi-reactor (CR) may be deployed as a capacity increase of the urea plant or as a reduction of the steam consumption of this urea plant if capacity is kept at the same level. In this example, this saves 100 kg of high-pressure steam (300° C. and 2.2 MPa absolute) per tonne of product produced.

TABLE 2

| Stream | Urea | $NH_3$ | $CO_2$ | $H_2O$ | Inert |
|---|---|---|---|---|---|
| USS | 35.5 | 29.5 | 16.5 | 18.5 | — |
| $CO_2$ | — | — | 96.0 | 0.5 | 3.5 |
| SUSS | 55.0 | 7.8 | 10.5 | 26.7 | — |
| SG | — | 40.0 | 54.0 | 3.5 | 2.5 |
| $NH_3$ | — | 99.6 | — | 0.4 | — |
| HPC | 23.5 | 34.5 | 26.0 | 16.0 | — |
| CRG | — | 56.0 | 37.0 | 2.5 | 4.5 |
| RG | — | 49.0 | 40.5 | 3.3 | 7.2 |
| EC | — | 39.0 | 39.0 | 22.0 | — |
| LPC | — | 30.0 | 37.0 | 33.0 | — |
| Inert | — | 5.5 | 5.0 | 0.5 | 89.0 |

What is claimed is:

1. Process for the preparation of urea from ammonia and carbon dioxide, wherein the preparation is effected wholly or partly in a vertical combi-reactor.

2. Process according to claim 1, wherein in the combi-reactor the condenser section is located beneath the reactor section and the scrubber section is placed above the reactor section.

3. Process according to claim 1, wherein the pressure in the combi-reactor is between 12 and 22 MPa and the temperature is between 150 and 250° C.

4. Process according to claim 1, wherein the gas stream leaving the stripper is fed to the condenser section of a vertical combi-reactor.

5. Process according to claim 1, wherein the gas stream which leaves the stripper is wholly or partially condensed in the carbamate stream which is transferred from the scrubber section to the condenser section via a downcomer.

6. Process according to claim 1, wherein the reactor section of the combi-reactor is provided with means which ensure that the liquid flows through the reactor substantially in plug flow.

7. Process according to claim 1, wherein the residence time of the reaction mixture in the combi-reactor is longer than 20 minutes.

8. Process according to claim 1, wherein the residence time of the reaction mixture in the, combi-reactor is shorter than 1 hour.

9. Process according to claim 1, wherein the combi-reactor is designed as a pipe having a diameter of between 1 and 5 meters and a length of between 5 and 60 m.

10. Process according to claim 1, wherein the number of compartments in the combi-reactor as series-arranged CSTRs is greater than 2.

11. Process according to claim 1, wherein the number of compartments in the combi-reactor as series-arranged CSTRs is less than 20.

12. Process according to claim 1, wherein the condensation zone and heat exchanger of the combi-reactor are designed as a submerged condenser.

13. Method of improving and optimising an existing urea plant, wherein a vertical combi-reactor is added.

14. Method according to claim 13, wherein, in a conventional urea plant, a stripper and gas/liquid separator are also added.

15. Method according to claim 13, wherein a combi-reactor is added in a urea stripping plant.

* * * * *